US008702795B2

(12) United States Patent
Shoji et al.

(10) Patent No.: US 8,702,795 B2
(45) Date of Patent: Apr. 22, 2014

(54) INTRAOCULAR LENS INSERTING DEVICE

(75) Inventors: Noriyuki Shoji, Kitamoto (JP);
Masanobu Inoue, Honjo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 13/059,401

(22) PCT Filed: Aug. 20, 2009

(86) PCT No.: PCT/JP2009/064549
§ 371 (c)(1),
(2), (4) Date: Mar. 2, 2011

(87) PCT Pub. No.: WO2010/021354
PCT Pub. Date: Feb. 25, 2010

(65) Prior Publication Data
US 2011/0270264 A1    Nov. 3, 2011

(30) Foreign Application Priority Data
Aug. 21, 2008   (JP) .................................. 2008-212409

(51) Int. Cl.
*A61F 9/007*   (2006.01)
*A61F 2/16*   (2006.01)

(52) U.S. Cl.
CPC ............. *A61F 2/1672* (2013.01); *A61F 2/1664* (2013.01); *A61F 2/167* (2013.01)
USPC ........................................ 623/6.12; 606/107

(58) Field of Classification Search
USPC ........................................ 606/107; 623/6.12
See application file for complete search history.

(56) References Cited

U.S. PATENT DOCUMENTS

| | | | |
|---|---|---|---|
| 2,761,446 | A | 9/1956 | Reed |
| 4,205,747 | A | 6/1980 | Gilliam et al. |
| 4,269,307 | A | 5/1981 | LaHaye |
| 4,423,809 | A | 1/1984 | Mazzocco |
| 4,573,998 | A | 3/1986 | Mazzocco |
| 4,608,049 | A | 8/1986 | Kelman |

(Continued)

FOREIGN PATENT DOCUMENTS

| | | |
|---|---|---|
| DE | 3610925 | 10/1987 |
| DE | 4110278 A | 10/1992 |

(Continued)

OTHER PUBLICATIONS

PCT International Search Report dated Sep. 15, 2009 for PCT App. Ser. No. PCT/JP09/64549.

*Primary Examiner* — Kathleen Holwerda
(74) *Attorney, Agent, or Firm* — Henricks, Slavin & Holmes LLP

(57) ABSTRACT

An intraocular lens insertion device (1) includes a main body (2), an operational portion (3) provided on an end (2a) of the main body (2), a knock mechanism (4) for moving the operational portion (3) forward and backward with respect to the main body (2), and a cartridge (5) attached to the other end (2b) of the main body (2) and serving as an insertion tube. The device is constructed, as a whole, such that the knock mechanism (4) moves the operational portion (3) repeatedly forward and backward so that an intraocular lens (6) placed in the cartridge (5) can be pushed out stepwise. The knock mechanism (4) is structured so as to move the operational portion (3) pushed forward toward a backward direction and automatically return it to an original position prior to the same being pushed forward.

13 Claims, 5 Drawing Sheets

(56) References Cited

U.S. PATENT DOCUMENTS

| | | | |
|---|---|---|---|
| 4,634,423 A | 1/1987 | Bailey | |
| 4,681,102 A | 7/1987 | Bartell | |
| 4,697,697 A | 10/1987 | Graham et al. | |
| 4,699,140 A | 10/1987 | Holmes | |
| 4,702,244 A | 10/1987 | Mazzocco | |
| 4,715,373 A | 12/1987 | Mazzocco et al. | |
| 4,747,404 A | 5/1988 | Jampel et al. | |
| 4,750,498 A | 6/1988 | Graham | |
| 4,759,359 A | 7/1988 | Willis et al. | |
| 4,763,650 A | 8/1988 | Hauser | |
| 4,765,329 A | 8/1988 | Cumming et al. | |
| 4,769,034 A | 9/1988 | Poley | |
| 4,781,719 A | 11/1988 | Kelman | |
| 4,787,904 A | 11/1988 | Severin | |
| 4,819,631 A | 4/1989 | Poley | |
| 4,834,094 A | 5/1989 | Patton | |
| 4,836,201 A | 6/1989 | Patton | |
| 4,862,885 A | 9/1989 | Cumming | |
| 4,880,000 A | 11/1989 | Holmes et al. | |
| 4,919,130 A | 4/1990 | Stoy | |
| 4,934,363 A | 6/1990 | Smith et al. | |
| 4,955,889 A | 9/1990 | Van Gent | |
| 4,976,716 A * | 12/1990 | Cumming | 606/107 |
| 4,988,352 A | 1/1991 | Poley | |
| 4,994,028 A | 2/1991 | Leonard et al. | |
| 5,066,297 A | 11/1991 | Cumming | |
| 5,098,439 A | 3/1992 | Hill et al. | |
| 5,123,905 A | 6/1992 | Kelman | |
| 5,139,501 A | 8/1992 | Klaas | |
| 5,171,241 A | 12/1992 | Buboltz et al. | |
| 5,176,686 A | 1/1993 | Poley | |
| 5,190,552 A | 3/1993 | Kelman | |
| 5,190,553 A | 3/1993 | Kanert et al. | |
| 5,222,972 A | 6/1993 | Hill et al. | |
| 5,242,450 A | 9/1993 | McDonald | |
| 5,259,395 A | 11/1993 | Li | |
| 5,275,604 A | 1/1994 | Rheinish et al. | |
| 5,281,227 A | 1/1994 | Sussman | |
| 5,304,182 A | 4/1994 | Rheinish et al. | |
| 5,354,333 A | 10/1994 | Kammann et al. | |
| 5,395,378 A | 3/1995 | McDonald | |
| 5,425,734 A | 6/1995 | Blake | |
| 5,454,818 A | 10/1995 | Hambleton et al. | |
| 5,468,246 A | 11/1995 | Blake | |
| 5,474,562 A | 12/1995 | Orchowski et al. | |
| 5,494,484 A | 2/1996 | Feingold | |
| 5,496,328 A | 3/1996 | Nakajima et al. | |
| 5,499,987 A | 3/1996 | Feingold | |
| 5,562,676 A | 10/1996 | Brady et al. | |
| 5,571,113 A | 11/1996 | McDonald | |
| 5,578,042 A | 11/1996 | Cumming | |
| 5,582,613 A | 12/1996 | Brady | |
| 5,582,614 A | 12/1996 | Feingold | |
| 5,584,304 A | 12/1996 | Brady | |
| 5,616,148 A | 4/1997 | Eagles et al. | |
| 5,620,450 A | 4/1997 | Eagles et al. | |
| 5,643,275 A | 7/1997 | Blake | |
| 5,643,276 A | 7/1997 | Zaleski | |
| 5,645,534 A | 7/1997 | Chanoch | |
| 5,653,715 A | 8/1997 | Reich et al. | |
| 5,653,753 A | 8/1997 | Brady et al. | |
| 5,702,402 A | 12/1997 | Brady | |
| 5,702,441 A | 12/1997 | Zhou | |
| 5,716,364 A | 2/1998 | Makker et al. | |
| 5,728,075 A | 3/1998 | Levander | |
| 5,728,102 A | 3/1998 | Feingold et al. | |
| 5,735,858 A | 4/1998 | Makker et al. | |
| 5,766,181 A | 6/1998 | Chambers | |
| 5,772,666 A | 6/1998 | Feingold et al. | |
| 5,772,667 A | 6/1998 | Blake | |
| 5,776,138 A * | 7/1998 | Vidal et al. | 606/107 |
| 5,800,442 A | 9/1998 | Wolf et al. | |
| 5,803,925 A | 9/1998 | Yang et al. | |
| 5,807,400 A | 9/1998 | Chambers et al. | |
| 5,810,833 A | 9/1998 | Brady et al. | |
| 5,810,834 A | 9/1998 | Heyman | |
| 5,860,984 A | 1/1999 | Chambers et al. | |
| 5,860,986 A | 1/1999 | Reich et al. | |
| 5,868,751 A | 2/1999 | Feingold | |
| 5,868,752 A | 2/1999 | Makker et al. | |
| 5,873,879 A | 2/1999 | Figueroa et al. | |
| 5,876,406 A | 3/1999 | Wolf et al. | |
| 5,876,407 A | 3/1999 | Makker et al. | |
| 5,876,440 A | 3/1999 | Feingold | |
| 5,891,152 A | 4/1999 | Feingold | |
| 5,902,307 A | 5/1999 | Feingold et al. | |
| 5,919,197 A | 7/1999 | McDonald | |
| 5,921,989 A | 7/1999 | Deacon et al. | |
| 5,928,245 A | 7/1999 | Wolf et al. | |
| 5,941,886 A | 8/1999 | Feingold | |
| 5,942,277 A | 8/1999 | Makker et al. | |
| 5,944,725 A | 8/1999 | Cicenas | |
| 5,947,974 A | 9/1999 | Brady et al. | |
| 5,947,975 A | 9/1999 | Kikuchi et al. | |
| 5,957,748 A | 9/1999 | Ichiha | |
| 6,001,107 A | 12/1999 | Feingold | |
| 6,010,510 A | 1/2000 | Brown et al. | |
| 6,022,358 A | 2/2000 | Wolf et al. | |
| 6,048,348 A | 4/2000 | Chambers et al. | |
| 6,051,000 A | 4/2000 | Heyman | |
| 6,056,757 A | 5/2000 | Feingold et al. | |
| 6,056,758 A | 5/2000 | Vidal et al. | |
| 6,059,791 A | 5/2000 | Chambers | |
| 6,074,397 A | 6/2000 | Chambers et al. | |
| 6,083,230 A | 7/2000 | Makker et al. | |
| 6,093,193 A | 7/2000 | Makker et al. | |
| 6,129,733 A | 10/2000 | Brady et al. | |
| 6,142,999 A | 11/2000 | Brady et al. | |
| 6,143,000 A | 11/2000 | Feingold | |
| 6,162,229 A | 12/2000 | Feingold et al. | |
| 6,174,315 B1 | 1/2001 | Chambers et al. | |
| 6,214,015 B1 | 4/2001 | Reich et al. | |
| 6,241,737 B1 | 6/2001 | Feingold | |
| 6,248,111 B1 | 6/2001 | Glick et al. | |
| 6,251,114 B1 | 6/2001 | Farmer et al. | |
| 6,254,607 B1 | 7/2001 | Makker et al. | |
| 6,267,768 B1 | 7/2001 | Deacon | |
| 6,283,975 B1 | 9/2001 | Glick et al. | |
| 6,283,976 B1 | 9/2001 | Portney | |
| 6,312,433 B1 | 11/2001 | Butts | |
| 6,334,862 B1 | 1/2002 | Vidal et al. | |
| 6,336,932 B1 | 1/2002 | Figueroa et al. | |
| 6,355,046 B2 | 3/2002 | Kikuchi et al. | |
| 6,371,960 B2 | 4/2002 | Heyman et al. | |
| 6,386,357 B1 | 5/2002 | Egawa | |
| 6,387,101 B1 | 5/2002 | Butts et al. | |
| 6,398,788 B1 | 6/2002 | Makker et al. | |
| 6,406,481 B2 | 6/2002 | Feingold et al. | |
| 6,428,545 B2 | 8/2002 | Portney | |
| 6,447,519 B1 | 9/2002 | Brady et al. | |
| 6,447,520 B1 | 9/2002 | Ott et al. | |
| 6,468,282 B2 | 10/2002 | Kikuchi et al. | |
| 6,471,708 B2 | 10/2002 | Green | |
| 6,491,697 B1 | 12/2002 | Clark et al. | |
| 6,497,708 B1 | 12/2002 | Cumming | |
| 6,500,181 B1 | 12/2002 | Portney | |
| 6,506,195 B2 | 1/2003 | Chambers et al. | |
| 6,537,283 B2 | 3/2003 | Van Noy | |
| 6,540,754 B2 | 4/2003 | Brady | |
| 6,554,839 B2 | 4/2003 | Brady | |
| 6,558,395 B2 | 5/2003 | Hjertman et al. | |
| 6,607,537 B1 | 8/2003 | Binder | |
| 6,629,979 B1 | 10/2003 | Feingold | |
| 6,666,871 B2 | 12/2003 | Kikuchi et al. | |
| 6,679,891 B2 | 1/2004 | Makker et al. | |
| 6,685,740 B2 | 2/2004 | Figueroa et al. | |
| 6,712,848 B2 | 3/2004 | Wolf et al. | |
| 6,723,104 B2 | 4/2004 | Ott | |
| 6,733,507 B2 | 5/2004 | McNicholas et al. | |
| 6,793,674 B2 * | 9/2004 | Zapata | 623/6.63 |
| 6,858,033 B2 | 2/2005 | Kobayashi | |
| 6,921,405 B2 | 7/2005 | Feingold et al. | |
| 6,923,815 B2 | 8/2005 | Brady et al. | |
| 6,976,989 B1 | 12/2005 | Vincent | |

(56) References Cited

U.S. PATENT DOCUMENTS

| | | |
|---|---|---|
| 7,014,641 B2 | 3/2006 | Kobayashi et al. |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,074,227 B2 | 7/2006 | Portney |
| 7,097,649 B2 | 8/2006 | Meyer |
| 7,131,976 B2 | 11/2006 | Kobayashi et al. |
| 7,156,854 B2 | 1/2007 | Brown et al. |
| 7,348,038 B2 | 3/2008 | Makker et al. |
| 7,422,604 B2 | 9/2008 | Vaquero et al. |
| 7,429,263 B2 | 9/2008 | Vaquero et al. |
| 7,458,976 B2 | 12/2008 | Peterson et al. |
| 7,476,230 B2 | 1/2009 | Ohno et al. |
| 7,494,505 B2 | 2/2009 | Kappelhof et al. |
| 7,645,300 B2 | 1/2010 | Tsai |
| 8,273,122 B2 | 9/2012 | Anderson |
| 8,382,769 B2 | 2/2013 | Inoue |
| 8,460,311 B2 | 6/2013 | Ishii |
| 8,470,032 B2 | 6/2013 | Inoue et al. |
| 8,475,528 B2 | 7/2013 | Ichinohe et al. |
| 8,523,877 B2 | 9/2013 | Ichinohe et al. |
| 8,523,941 B2 | 9/2013 | Ichinohe et al. |
| 8,535,375 B2 | 9/2013 | Ichinohe et al. |
| 8,545,512 B2 | 10/2013 | Ichinohe et al. |
| 8,574,239 B2 | 11/2013 | Ichinohe et al. |
| 8,603,103 B2 | 12/2013 | Kudo et al. |
| 2001/0007942 A1 | 7/2001 | Kikuchi et al. |
| 2002/0103490 A1 | 8/2002 | Brady |
| 2002/0151904 A1 | 10/2002 | Feingold et al. |
| 2002/0165610 A1 | 11/2002 | Wadlaock |
| 2002/0193805 A1 | 12/2002 | Ott et al. |
| 2003/0036765 A1 | 2/2003 | Van Noy |
| 2003/0040755 A1 | 2/2003 | Meyer |
| 2003/0050647 A1 | 3/2003 | Brady |
| 2003/0088253 A1 | 5/2003 | Seil |
| 2003/0139749 A1 | 7/2003 | Kikuchi et al. |
| 2003/0181921 A1 | 9/2003 | Jeannin |
| 2003/0195522 A1 | 10/2003 | McNicholas |
| 2003/0212406 A1 | 11/2003 | Kobayashi et al. |
| 2003/0212407 A1 | 11/2003 | Kikuchi |
| 2003/0212409 A1 | 11/2003 | Kobayashi et al. |
| 2004/0111094 A1 | 6/2004 | Meyer |
| 2004/0117012 A1 | 6/2004 | Vincent |
| 2004/0238392 A1 | 12/2004 | Peterson et al. |
| 2004/0243141 A1 | 12/2004 | Brown et al. |
| 2005/0033308 A1 | 2/2005 | Callahan et al. |
| 2005/0049605 A1 | 3/2005 | Vaquero et al. |
| 2005/0049606 A1 | 3/2005 | Vaquero |
| 2005/0125000 A1 | 6/2005 | Tourrette et al. |
| 2005/0143750 A1 | 6/2005 | Vaquero |
| 2005/0182419 A1 | 8/2005 | Tsai |
| 2005/0222578 A1 | 10/2005 | Vaquero |
| 2005/0261703 A1 | 11/2005 | Feingold et al. |
| 2006/0085013 A1* | 4/2006 | Dusek et al. ................ 606/107 |
| 2006/0142781 A1 | 6/2006 | Pynson et al. |
| 2006/0167466 A1 | 7/2006 | Dusek |
| 2006/0229633 A1 | 10/2006 | Shepherd |
| 2006/0235429 A1 | 10/2006 | Lee et al. |
| 2006/0293694 A1 | 12/2006 | Futamura |
| 2008/0033449 A1 | 2/2008 | Cole et al. |
| 2008/0058830 A1 | 3/2008 | Cole et al. |
| 2008/0086146 A1 | 4/2008 | Ishii et al. |
| 2008/0097459 A1 | 4/2008 | Kammerlander et al. |
| 2008/0221584 A1 | 9/2008 | Downer |
| 2009/0036898 A1 | 2/2009 | Ichinohe |
| 2009/0043313 A1 | 2/2009 | Ichinohe |
| 2009/0112223 A1 | 4/2009 | Downer et al. |
| 2009/0125034 A1 | 5/2009 | Pynson |
| 2009/0138022 A1 | 5/2009 | Tu et al. |
| 2009/0204122 A1 | 8/2009 | Ichinohe et al. |
| 2009/0216244 A1 | 8/2009 | Pynson |
| 2009/0248031 A1 | 10/2009 | Ichinohe |
| 2010/0161049 A1 | 6/2010 | Inoue |
| 2010/0185206 A1 | 7/2010 | Ichinohe et al. |
| 2010/0217273 A1 | 8/2010 | Someya et al. |
| 2010/0286704 A1 | 11/2010 | Ichinohe et al. |
| 2011/0082463 A1 | 4/2011 | Inoue |
| 2011/0098717 A1 | 4/2011 | Inoue |
| 2011/0264101 A1 | 10/2011 | Inoue et al. |
| 2011/0288557 A1 | 11/2011 | Kudo et al. |
| 2012/0022549 A1 | 1/2012 | Someya et al. |
| 2012/0071887 A1 | 3/2012 | Ichinohe et al. |
| 2013/0006259 A1 | 1/2013 | Sanger |
| 2013/0018460 A1 | 1/2013 | Anderson |
| 2013/0226193 A1 | 8/2013 | Kudo et al. |
| 2013/0245635 A1 | 9/2013 | Inoue |

FOREIGN PATENT DOCUMENTS

| | | |
|---|---|---|
| EP | 0363213 | 4/1990 |
| EP | 0727966 | 9/2003 |
| EP | 1832247 A1 | 9/2007 |
| EP | 1338254 | 12/2008 |
| FR | 2749752 A | 12/1997 |
| JP | 63-197453 A | 8/1988 |
| JP | 04-212350 A | 8/1992 |
| JP | 5-103808 | 4/1993 |
| JP | 5-103809 | 4/1993 |
| JP | 8-024282 A | 1/1996 |
| JP | 8-505540 | 6/1996 |
| JP | 9-506285 A | 6/1997 |
| JP | 11-113939 A | 4/1999 |
| JP | 11-506357 A | 6/1999 |
| JP | 11-506357 A | 6/1999 |
| JP | 2000-516487 A | 12/2000 |
| JP | 2001-502563 | 2/2001 |
| JP | 2001-502563 | 2/2001 |
| JP | 2001-104347 A | 4/2001 |
| JP | 2002-516709 A | 6/2002 |
| JP | 2002-355268 A | 12/2002 |
| JP | 2002-541912 A | 12/2002 |
| JP | 2003-144480 A | 5/2003 |
| JP | 3412106 B2 | 6/2003 |
| JP | 2003-210498 A | 7/2003 |
| JP | 2003-325569 A | 11/2003 |
| JP | 2003-325570 A | 11/2003 |
| JP | 2003-325572 A | 11/2003 |
| JP | 2004-024854 A | 1/2004 |
| JP | 2004-188194 A | 7/2004 |
| JP | 2004-351196 A | 12/2004 |
| JP | 2004-351196 A | 12/2004 |
| JP | 2008-521535 A | 6/2006 |
| JP | 2006-181269 A | 7/2006 |
| JP | 2006-297146 A | 11/2006 |
| JP | 2006-333924 A | 12/2006 |
| JP | 2006-333981 A | 12/2006 |
| JP | 2007-503872 A | 3/2007 |
| JP | 2007-152010 A | 6/2007 |
| JP | 2007-181604 A | 7/2007 |
| JP | 2007-526091 A | 9/2007 |
| JP | 2008-521535 A | 6/2008 |
| JP | 2008-212689 A | 9/2008 |
| WO | WO9407436 A1 | 4/1994 |
| WO | WO9513022 A1 | 5/1995 |
| WO | WO 96/28122 A1 | 9/1996 |
| WO | WO9715253 A1 | 5/1997 |
| WO | WO9812969 A1 | 4/1998 |
| WO | WO9958086 A1 | 11/1999 |
| WO | WO9959668 A1 | 11/1999 |
| WO | WO0045746 A1 | 8/2000 |
| WO | WO0062712 A1 | 10/2000 |
| WO | WO02071982 A1 | 9/2002 |
| WO | WO02096322 A1 | 12/2002 |
| WO | WO2005023154 A1 | 3/2005 |
| WO | WO2005070341 A1 | 8/2005 |
| WO | WO2005084588 A1 | 9/2005 |
| WO | WO2006070628 A1 | 7/2006 |
| WO | WO2006080191 A1 | 8/2006 |
| WO | WO2006090531 A1 | 8/2006 |
| WO | WO 2007/097221 A1 | 4/2007 |
| WO | WO2007037223 A1 | 4/2007 |
| WO | WO2007080869 A1 | 7/2007 |
| WO | WO2008149794 A1 | 12/2008 |
| WO | WO2008149795 A1 | 12/2008 |

(56) References Cited

FOREIGN PATENT DOCUMENTS

| WO | WO2009058929 | A1 | 7/2009 |
| WO | WO2009148091 | A1 | 12/2009 |
| WO | WO2011126144 | A1 | 10/2011 |
| WO | WO2011155636 | A1 | 12/2011 |

* cited by examiner

INTRAOCULAR LENS INSERTING DEVICE

TECHNICAL FIELD

The present invention relates to an intraocular lens inserting device used for inserting an intraocular lens into an aphakic eye that has undergone a cataract surgery or a phakic eye in a refractive surgery.

BACKGROUND ART

In these days, with phacoemulsification and the like prevailing, an intraocular lens available for being inserted from a small incision, namely a foldable intraocular lens made of a soft material such as silicone, soft acrylic, or hydrogel, has been developed and used widely in clinical practice with an aim to reduce postoperative astigmatism and realize minimally invasive surgery.

On the other hand, there have also been developed a variety of intraocular lens inserting devices as a surgical instrument for inserting such foldable intraocular lens into an eye from an even smaller incision. According to such intraocular lens inserting devices, a folded intraocular lens can be pushed out into an eye through a tubular cylindrical insertion portion, thereby allowing the intraocular lens to be inserted into an eye from a substantially smaller incision compared to using conventional methods which use a pair of tweezers to insert an intraocular lens into an eye.

Such intraocular lens inserting devices are classified broadly into two types: one is a screwed type (screw-in type); the other is a push-in type.

The push-in type is one type of an intraocular lens inserting device in which an operator presses an operational portion of the device against a resistance such as a friction between an intraocular lens and the inner wall of a cylindrical insertion portion, and the pressure applied at that time is transferred to the intraocular lens, thereby advancing the intraocular lens (For example, see Patent Documents 1, 2 and 3). According to these push-in type intraocular lens inserting devices, operation for inserting the intraocular lens is simple and possible with one hand. Thus, the push-in type intraocular lens inserting device has the advantage that an operator can perform another operation with his/her other hand during the insertion operation. On the other hand, the push-in type intraocular lens inserting devices have such a problem that it is comparatively difficult to control an operational pressure applied to push the operational portion because the operator has to move the intraocular lens forward while keeping the balance between the friction of the intraocular lens with the inner wall of the cylindrical insertion portion and the operational pressure of the operational portion. Further, since a nozzle provided on the leading end of the intraocular lens inserting device is generally the thinnest part of the cylindrical insertion portion the intraocular lens passes through, a load applied to the intraocular lens becomes large when a high-degree thick intraocular lens is released from the nozzle or when an inner diameter of a nozzle is made smaller in order to match a smaller incision, thus leading to the possibilities that the intraocular lens may be unexpectedly released into an eye to thereby damage an ocular tissue.

As for a screwed type intraocular lens inserting device, the relation between its plunger and main body is similar to that between a male screw and a female screw, and an operational portion provided at one end of the plunger is rotated, thus moving the plunger, or a rod for pushing out the intraocular lens, toward the lens advancing direction, thereby advancing the intraocular lens (For example, see Patent Document 4). According to these screwed type intraocular lens inserting devices, travel distance of the plunger or rod can be easily controlled, and thus it has the advantage of being able to prevent the intraocular lens from being unexpectedly released into an eye even in the case that a load applied when the intraocular lens passes through the nozzle becomes large, such as when the intraocular lens with a thick optical portion is released, or the nozzle is formed to have a smaller inner diameter. On the other hand, the screwed type intraocular lens inserting device requires the inserting operation to be performed with both hands, and thus there are concerns that an operation of the device becomes somewhat intricate compared to the push-in type intraocular lens inserting device.

Patent Document 1: Japanese Unexamined Patent Application Publication No. 2000-516487
Patent Document 2: Japanese Unexamined Patent Application Publication No. 2003-144480
Patent Document 3: Japanese Unexamined Patent Application Publication No. 2004-351196
Patent Document 4: Japanese Unexamined Patent Application Publication No. H11-506357

DISCLOSURE OF THE INVENTION

Problem to be Solved by the Invention

There is proposed a method in which a "spring" is used as a means to reduce "the difficulties in controlling the operational pressure" recognized as a problem with the push-in type intraocular lens inserting devices (Japanese Unexamined Patent Application Publication No. 2000-516487). This is an attempt to make it sensuously easier to control the operational pressure of the operational portion by adding a potential resistive force against the operational pressure using the spring to thereby balance the repulsive force of the spring and the friction of the intraocular lens with the operational pressure. Even if this approach is used, however, it does not suffice yet for an operator to have full control of the operational pressure, and hence, many operators still use the screwed type intraocular lens inserting device that has a less need for controlling the operational pressure, although the operation thereof is rather complicated.

In view of the problem above, it is, therefore, an object of the present invention to provide an intraocular lens inserting device enabling an operator to easily control the operational pressure of the operational portion.

Means to Solve the Problem

The invention according to a first aspect of the present invention is an intraocular lens inserting device having an operational portion to be pressed to push out an intraocular lens, characterized in comprising:

a knock mechanism for allowing said pressed operational portion to automatically return to a position where said operational portion is operable.

The invention according to a second aspect of the present invention is characterized in further comprising:

a lens contact portion for pushing out the intraocular lens;

a transmitting portion for transmitting an external force applied to said operational portion to said lens contact portion;

an insertion tube for releasing said intraocular lens pushed out by said lens contact portion to an outside, wherein said knock mechanism comprises:

a stopping means for temporarily stopping said lens contact portion before the intraocular lens is completely released out to the outside after said lens contact portion starts pushing out the intraocular lens; and a returning means for allowing said operational portion to return to a position where said operational portion is operable, with said lens contact portion being temporarily stopped by said stopping means.

The invention according to third and fourth aspects of the present invention is characterized in further comprising:

a main body for fixing said insertion tube in a position anterior thereto, wherein said operational portion is provided in a position posterior to said main body.

The invention according to a fifth aspect of the present invention is characterized in that said intraocular lens is of a preset type in which said intraocular lens is set beforehand.

The invention according to a sixth aspect of the present invention is characterized in that said returning means is a coil spring for biasing said operational portion toward a backward direction.

The invention according to a seventh aspect of the present invention is characterized in that said stopping means allows said lens contact portion to stop at least once when said intraocular lens passes through an inside of a nozzle provided at a leading end of said insertion tube.

Effect of the Invention

According to the intraocular lens inserting device of the present invention, the operational pressure of the operational portion can be easily controlled by a knock mechanism allowing the pressed operational portion to automatically return to the position where the intraocular lens inserting device is operable.

BEST MODE FOR CARRYING OUT THE INVENTION

First Embodiment (1) Entire Structure

Figure 1:
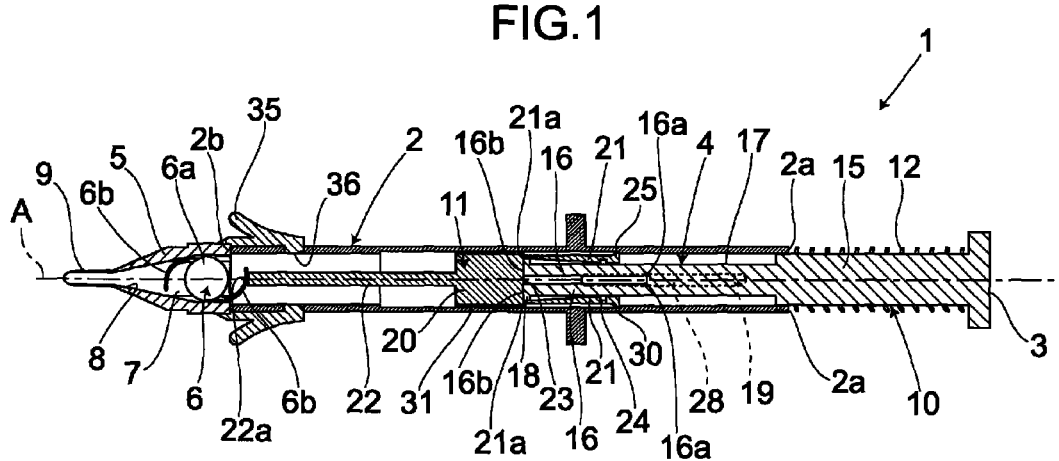
FIG. 1 is a cross-sectional view showing the overall structure of an intraocular lens inserting device according to a first embodiment of the invention.

An intraocular lens inserting device 1 shown in FIG. 1 comprises a main body 2, an operational portion 3 provided on one end 2a of the main body 2, a knock mechanism allowing the operational portion 3 to move back and forth against the main body 2, and a cartridge 5 attached to an other end 2b of the main body 2. The intraocular lens inserting device 1 allows the operational portion 3 to move back and forth repeatedly as a whole due to its knock mechanism 4 so that an intraocular lens 6 placed in the cartridge 5 can be pushed out in a stepwise fashion. It is to be noted herein that a disposable inserting tubular portion in which an intraocular lens is placed by an operator or his/her assistant during the surgery is generally called a cartridge.

The intraocular lens 6 is made of a soft material such as silicone, soft acrylic hydrogel or the like, which is released into the eye and then expanded therein to function as a substitute for a crystalline lens, and comprises, for example, an optical portion 6a and two support portions 6b, 6b.

In the following description, a lens advancing direction (push-out direction) is called "forward" and the opposite direction against the lens advancing direction is called "backward".

The knock mechanism 4 is constituted such that it allows the intraocular lens 6 to be pushed out a predetermined distance by pushing the operational portion 3 forward and at the same time, it allows the operational portion 3 thus pushed forward to be automatically moved backward. The knock mechanism 4 comprises a plunger 10 as a transmitting portion integrated with the operational portion 3, a rod 11, a coil spring 12 as a returning means biasing the plunger 10 backward, and a hereafter-described engaging portion provided on the inner surface of the main body 2.

It is noted herein that the main body 2, plunger 10 and rod 11 are preferably made of synthetic resin capable of being injection molded. This enables mass production of the main body 2, plunger 10 and rod 11 at low costs, allowing the device of the present invention to be suitably applied to disposable ones.

The plunger 10 functions not only to limit a movable range of the operational portion 3 to a predetermined range but also to transmit, as a pressure transmitting means, an external force applied to the operational portion 3 by the operator to a lens contact portion 22a provided on a leading end of a push-out shaft 22 of the rod 11. The plunger 10 comprises an axial body 15 provided with the operational portion 3 on one end thereof and a pair of push-out pieces 16, 16 formed on the other end thereof. The operational portion 3 is formed in the shape of disk by expanding the diameter of the one end of the axial body 15 concentrically and is integrated with the axial body 15.

The axial body 15 is loaded with the coil spring 12 and is movably inserted into the main body 2. The pair of the push-out pieces 16, 16 is provided on the other end of the axial body 15 through a connecting portion 17. The connecting portion 17 has a stopper pin 19 protruded in a direction perpendicular to the lens advancing axis A.

The pair of the push-out pieces 16, 16 is provided on both sides with the lens advancing axis A disposed therebetween, and is formed substantially parallel to the lens advancing axis A in such a way that a leading end of the connecting portion 17 is bifurcated. The pair of the push-out pieces 16, 16 is also provided so as to be elastically deformable in the direction perpendicular to the lens advancing direction A with base ends 16a, 16a connected to the connecting portion 17 being the center of rotation. Also, a convex portion 18 protruded outward is formed at a leading end 16b of each push-out piece 16.

The rod 11 is structured so as to be separate from the plunger 10, namely not integrated with the plunger 10, and allows the intraocular lens 6 to be pushed out by the external force transmitted from the plunger 10. The rod 11 comprises a sliding body 20, a pair of locking pieces 21, 21 provided on one end of the sliding body 20, the push-out shaft 22 provided on an other end of the sliding body 20. Incidentally, any known shape may be employed for the shape of the lens contact portion 22a provided on the leading end of the push-out shaft 22 of the rod 11.

The sliding body 20 is made of a cylindrical member having such an external diameter that allows the same to be movably inserted into the main body 2 and is structured so as to hold the push-out shaft 22 on the lens advancing axis A. The sliding body 20 has an abutting surface 23 at one end thereof, which is substantially flat and is perpendicular to the lens advancing axis A.

The pair of the locking pieces 21, 21 is provided on both sides with respect to the lens advancing axis A and is formed to extend substantially parallel to the lens advancing axis A from the vicinity of the outer edge of the sliding body 20. Further, the pair of locking pieces 21, 21 is formed tapered from a leading end toward a support end 21a of the sliding body 20 and is provided so as to be elastically deformable (or "deflectable") toward the direction perpendicular to the lens advancing direction A with the support end 21a being the center of pivotal rotation. Furthermore, the leading end of each deflectable locking piece 21 is formed at its inside with a concave portion 24 to be engaged with the convex portion 18, while a protrusion 25 is formed at its outside, respectively. The deflectable locking pieces 21 and protrusions 25 define a pair of latches that releasably connect the rod 11 to the main body 2, in the manner described below, when the rod 11 is in the pre-use position.

Also, the cartridge 5 is provided with a lens placement portion 7, a transition portion 8 and a nozzle 9 in sequence along the lens advancing axis A so that the intraocular lens 6 placed on the lens placement portion 7 is pushed out therefrom by the rod 11 to pass through the transition portion 8, thereby allowing the intraocular lens 6 to be folded small and then released from the nozzle 9 to the outside with the lens being folded small.

Further, both sides of the cartridge 5 are each formed with a wing 35 which is elastically deformable in the direction perpendicular to the lens advancing axis A. Each wing 35 is formed, at an inside of its back end, with an engagement protrusion 3. The cartridge 5 is constituted such that the back end of each wing 35 is elastically deformed outward when an external force from the outside toward the inside thereof is applied to the leading end of the wing 35.

Figure 2:
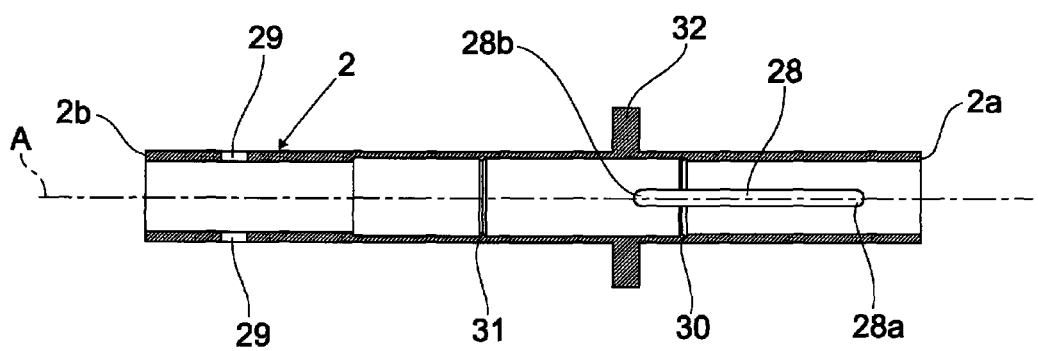
FIG. 2 is a cross-sectional view showing the structure of a main body according to the first embodiment.

As shown in FIG. 2, the main body 2 is made of the cylindrical member and is provided with a sliding hole 28 on the surface of the one end 2a, said sliding hole 28 being oval-shaped, extending parallel to the lens advancing direction A to serve as a stopping means. Further, the surface at the other end 2b of the main body 2 is formed with rectangular receiving holes 29, 29 on both sides with respect to the lens advancing direction A so that they may be engaged with the engagement protrusions 36 of the cartridge 5.

Moreover, the main body 2 is provided on its inner circumferential surface with a fixing concave portion 30 for fixing the rod 11 as the aforesaid engaging portion and a regulating convex portion 31 for regulating the rod 11 so as not to move backward. In addition, a finger catching portion 32 is protruded outward on the outer surface of the main body 2.

According to the intraocular lens inserting device 1 with each part structured as above, first, the rod 11 and the plunger 10 in which the coil spring 12 is loaded are inserted into the main body 2 in sequence and then the knock mechanism 4 is attached to the main body 2. Note that when the rod 11 is inserted into the main body 2, the push-out shaft 22 of the rod 11 is first inserted into the one end 2a of the main body 2 and then it is inserted deeper up to a position where the protrusion 25 of the locking piece 21 engages with the fixing concave portion 30 of the main body 2.

Figure 3:
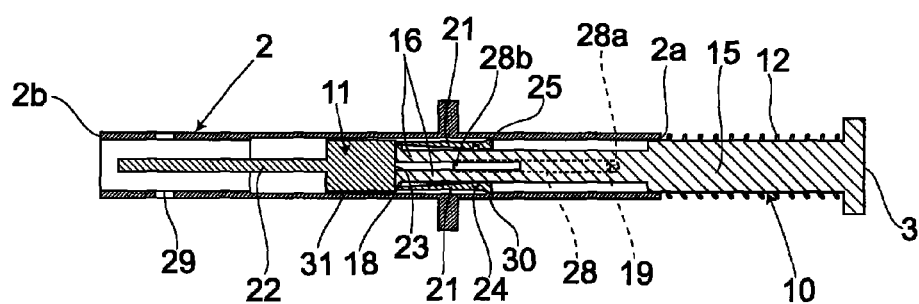
FIG. 3 is a cross-sectional view showing the main body with a knock mechanism according to the first embodiment.

After that, the push-out piece 16 of the plunger 10 loaded with the coil spring 12 is inserted into the one end 2a of the main body 2. At this time, the plunger 10 is inserted further into the main body 2 up to a position where the push-out piece 16, passing through between the locking pieces 21, 21 has its leading end 16b abutted on an abutting surface 23 (FIG. 3).

Also, the stopper pin 19 provided on the connecting portion 17 of the plunger 10 is movably inserted into the sliding hole 28 of the main body 2. In this way, the plunger 10 becomes movable back and forth in a range of from a position where the stopper pin 19 abuts on one end 28a of the sliding hole 28 to another position where it abuts on the other end 28b thereof. Thus, the operational portion 3 becomes capable of moving back and forth in parallel to the lens advancing axis A.

Incidentally, in the subsequent description, the position of the operational portion 3 (plunger 10) where the stopper pin 19 abuts on the one end 28a of the sliding hole 28 is called "origin", and the position of the operational portion 3 (plunger 10) where the stopper pin 19 abuts on the other end 28b of the sliding hole 28 is called "push-out position".

Additionally, the coil spring 12 is loaded between the one end 2a of the main body 2 and the operational portion 3 to bias the operational portion 3 toward the backward direction, and hence, when the operational portion 3 is moved forward, the coil spring 12 is capable of allowing the operational portion 3 to return to an operable position.

The term "operable position" means a position where an operator is enabled to plunge the operational portion 3 in the forward direction. In this embodiment, such operable position is the one where the stopper pin 19 is away from the other end 28b toward the one end 28a of the sliding hole 28. Therefore, the operable position is not limited to the position where the stopper pin 19 abuts on the one end 28a of the sliding hole 28.

Then, the cartridge 5 in which the intraocular lens 6 is placed is attached to the main body 2 with the knock mechanism 4 mounted in the foregoing manner. The cartridge 5 is capable of allowing the other end 2b of the main body 2 to be inserted thereinto because the back ends of the wings 35 are elastically deformed outwards by applying an external force to the leading ends of the wings 35 from the outside thereof to the inside thereof. Under that condition, when the external force applied to the leading ends of the wings 35 is released, the cartridge 5 is detachably fixed to the main body 2 in such a way that an engagement protrusion 36 is engaged with a receiving hole 29 by elastic return of the wings 35. Incidentally, as preparation for starting the operation of the device 1, generally, a certain liquid enabling the smooth movement of the intraocular lens 6 such as a viscoelastic material or the like, is injected into the inside of the cartridge 5 before the cartridge 5 is attached to the main body 2.

From the above-described, there can be obtained the intraocular lens inserting device 1 of the invention, allowing the intraocular lens 6 to be pushed out by the knock mechanism 4 so that it can be released from the cartridge 5 toward the outside with the intraocular lens 6 being folded small.

(2) Operations and Effects

Figure 4A:
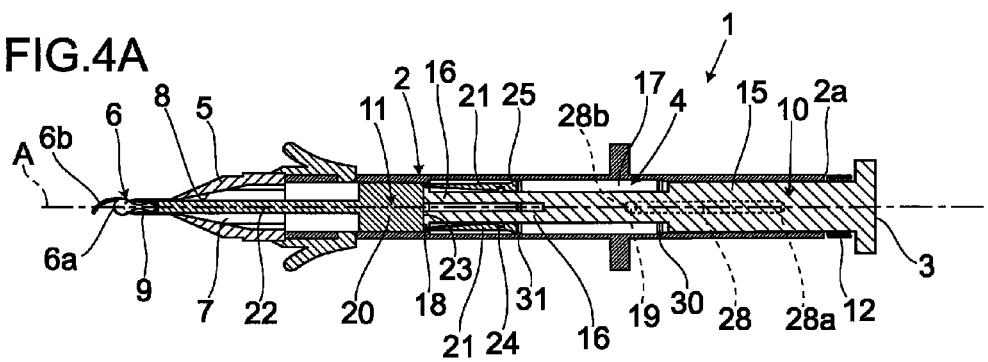
FIG. 4 is a diagram showing the intraocular lens inserting device in use in a stepwise manner according to the first embodiment, in which (a) is a section thereof illustrating the first push-out operation thereof, (b) illustrating a return to a position where the intraocular lens inserting device is operable, and (c) illustrating the second push-out operation thereof, respectively.

According to the foregoing structure, when the operational portion 3 positioned at the origin position (FIG. 1) is plunged into the main body 2 from this position, the engagement between the protrusion 25 and the fixing concave portion 30 of the main body 2 is released by an external force applied to the operational portion 3 toward the forward direction. And then, as shown in FIG. 4(a), the plunger 10 and the rod 11 moves together in the forward direction while compressing the coil spring 12.

At this moment, the plunger 10 allows the stopper pin 19 to move from the one end 28a toward the other end 28b within the sliding hole 28 provided in the main body 2. Thus, the plunger 10 and the rod 11 allow the stopper pin 19 to be able to freely move in a reciprocal manner a distance corresponding to the length from the one end 28a of the sliding hole 28 to the other end 28b thereof. In this way, due to the stopper pin 19 of the plunger 10 reaching the other end 28b of the sliding hole 28 of the main body 2, the plunger 10 and the operational portion 3 are allowed to mechanically stop at the push-out position. Thus, the plunger 10 and operational portion 3 become unable to move in the forward direction.

At this time, while the rod 11 moves in the forward direction, the protrusion 25 is allowed to overcome the regulating convex portion 31 of the main body 2 in such a way that the locking pieces 21, 21 elastically deform toward the inside with respect to the lens advancing axis A.

Figure 4B:
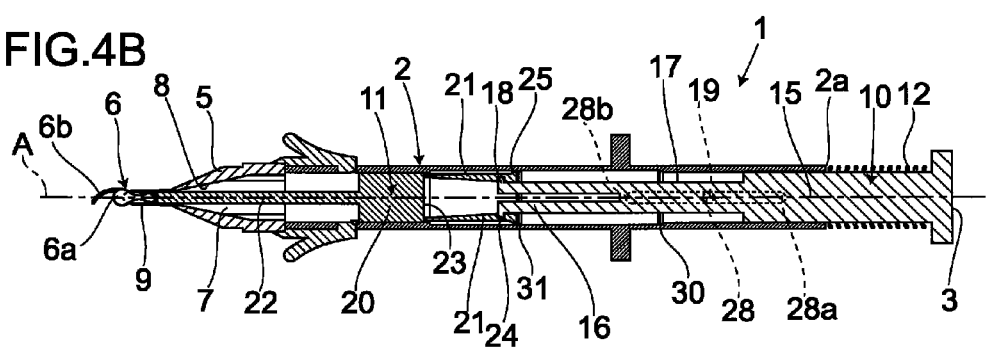

Then, when the external force applied to the operational portion 3 is released, as shown in FIG. 4(b), the plunger 10 is allowed to move in the backward direction by the biasing force of the coil spring 12. At this stage as well, the stopper pin 19 moves within the sliding hole 28 from the other end 28b (push-out position) to the one end 28a in the plunger 10.

In this way, when the operational portion 3 moves from the push-out position toward the one end 28a, the push-out piece 16 moves inside of the locking pieces 21, 21 in the backward direction. On the other hand, the backward movement of the rod 11 is regulated since the protrusions 25 of the locking pieces 21, 21 engage with the regulating convex portions 31 of the main body 2, and thus it is kept stopped. Then, the convex portion 18 of the push-out piece 16 is engaged with the concave portion 24 of each locking piece 21. In this manner, the plunger 10 and the operational portion 3 return to the operable position.

Through the first operation described above, the rod 11 allows the lens contact portion 22a provided on the leading end of the push-out shaft 22 to abut on a circumference of the optical portion 6a of the intraocular lens 6 placed in the cartridge 5 to thereby push out the intraocular lens 6 in the forward direction. According to the present embodiment, the intraocular lens inserting device 1 permits the lens contact portion 22a to stop temporarily when the intraocular lens 6 passes through the inside of the nozzle 9. This causes the intraocular lens 6 to move from the lens placement portion 7, through the transition portion 8 up to the nozzle 9 in sequence and to stop at a predetermined position. The term "predetermined position" here means the position where the intraocular lens 6 is about to be released from the nozzle 9 of the cartridge 5. Therefore, the intraocular lens 6 at the predetermined position is in such a state that it can be completely released to the outside if only a slight additional force is applied.

Figure 4C:
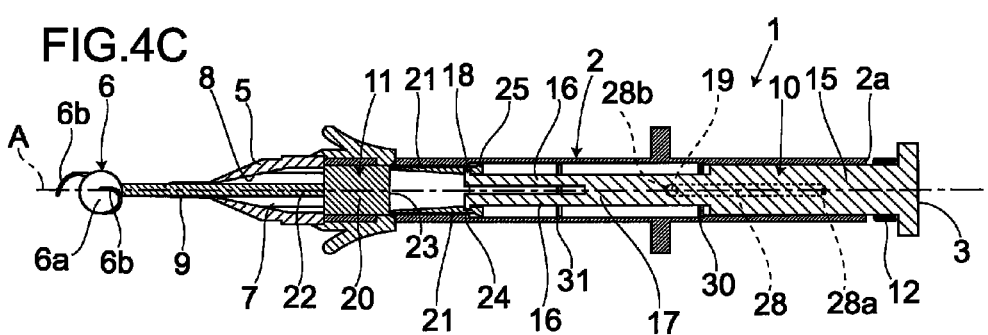

Next, as shown in FIG. 4(c), when the operational portion 3 returned back to the operable position is plunged again into the main body 2, the plunger 10 and the rod 11 are allowed to move together in the forward direction, since the convex portions 18 of the push-out piece 16 are engaged with the concave portions 24 of the locking pieces 21, 21.

At this stage as well, the stopper pin 19 of the plunger 10 moves from the operable position toward the other end 28b within the sliding hole 28 provided in the main body 2. Thus, when the stopper pin 19 reaches the other end 28b of the sliding hole 28, the plunger 10 then mechanically stops at the push-out position.

In this way, through the second operation of plunging the operational portion 3 returned back to the operable position into the main body 2 again, the push-out shaft 22 releases the intraocular lens 6 from the nozzle 9 to the outside. At this time, the lens contact portion 22a of the push-out shaft 22 is brought into a position protruded from the nozzle 9, enabling the adjustment of the position of the intraocular lens 6 and its supporting portions 6b, 6b released into the eye.

The intraocular lens inserting device 1 according to the present embodiment comprises the knock mechanism 4 automatically returning the operational portion 3 operable to push out the intraocular lens 6 to the operable position. This facilitates the control of the operational pressure of the operational portion 3 because the operator does not need to plunge the lens at a time in performing the operation for pushing out the intraocular lens 6 for such a long distance for a stroke from the position where the intraocular lens 6 is placed to the position where it is released. In addition, when operating the intraocular lens inserting device 1 by one hand, it is possible to shorten a distance for one stroke for pushing out the intraocular lens 6 at one time, thereby leading to easier operation by one hand.

Further, according to the present embodiment, the intraocular lens inserting device 1 is constituted so as to release the intraocular lens 6 to the outside by pushing out the operational portion 3 in the forward direction twice. Accordingly, the travel distance of the operational portion 3 can be reduced compared to the conventional devices which release the intraocular lens 6 to the outside by one-time push-out operation, enabling the operator to easily adjust the travel distance of the intraocular lens 6.

Furthermore, the intraocular lens inserting device 1 is constituted such that in the first push-out operation, the intraocular lens 6 is mechanically stopped just before the intraocular lens 6 is about to be released from the nozzle 9 of the cartridge 5, thereby enabling an operator to be prevented from unexpected release of the intraocular lens 6 into an eye without requiring any particular skills. Specifically, when the intraocular lens 6 passes through the nozzle 9, the operational portion 3 needs to be plunged hard toward the forward direction in order to push out the intraocular lens 6 because the intraocular lens 6 is folded small. However, in the first push-out operation, the intraocular lens inserting device 1 is allowed to mechanically stop the intraocular lens 6 just before the lens 6 is about to be released from the nozzle 9 of the cartridge 5, so that the intraocular lens 6 is prevented from being unexpectedly released into an eye even if a force to plunge the operational portion 3 is strong, thereby safely releasing the intraocular lens 6.

Moreover, even in the second push-out operation in which it is necessary to plunge the operational portion 3 hard, the intraocular lens inserting device 1 allows the operational portion 3 to automatically return to the operable position, so that the operator can operate the operational portion 3 at the same operable position as at the first operation. Therefore the operator can more easily insert the intraocular lens 6 into an eye.

Additionally, according to the present embodiment, the operational portion 3 is provided on the other end 2a of the main body 2, and thus the operation of inserting the intraocular lens 6 becomes easy, thus enabling the intraocular lens inserting device 1 to be operated by one hand. Therefore, the operator can perform another operation by the other hand during the inserting operation of the intraocular lens 6.

In addition, according to the present embodiment, the operational portion 3 is biased toward the backward direction by the coil spring 12, the operational portion 3 can be allowed to return to the operable position more reliably.

2. Second Embodiment (1) Entire Structure

An intraocular lens inserting device 40 according to the present embodiment is different from the device of the foregoing first embodiment which releases the intraocular lens to the outside by performing the operations for plunging the operational portion into the main body twice, in that it releases the intraocular lens to the outside by performing such operations three times. Incidentally, in the present embodiment, the same elements as those in the first embodiment are denoted by the same reference numerals, and their duplicate descriptions are omitted.

Figure 5:
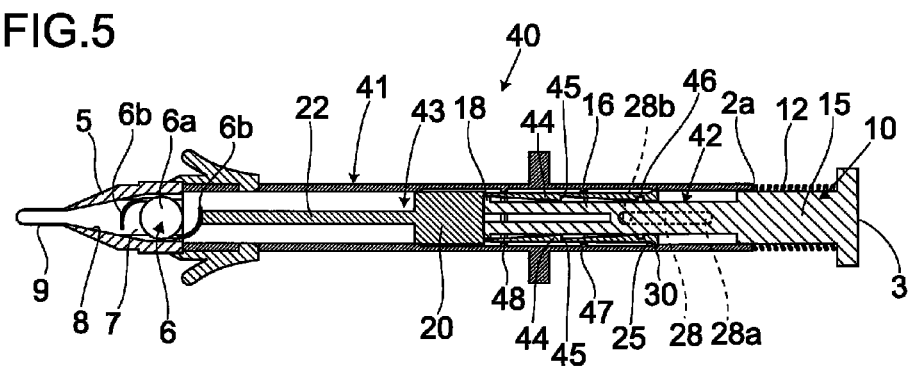
FIG. 5 is a cross-sectional view showing the overall structure of an intraocular lens inserting device according to a second embodiment of the invention.

The intraocular lens inserting device 40, as shown in FIG. 5, comprises a main body 41, an operational portion 3, a knock mechanism 42 and the cartridge 5, and it is constituted as a whole such that it may push out the intraocular lens 6 placed in the cartridge 5 in a stepwise fashion by moving the operational portion 3 back and forth repeatedly using the knock mechanism 42.

The knock mechanism 42 includes the plunger 10, a rod 43, the coil spring 12 biasing the plunger 10 toward the retracting or backward direction, and engaging portions (described later) provided on an inner surface of the main body 41.

The rod 43 comprises a sliding body 20, a pair of locking pieces 44 and a push-out shaft 22 provided on an other end of the sliding body 20. A first concave portion 45 and a second concave portion 46 with which the aforesaid convex portion engages are provided on an inner side of a leading end of each locking piece 44, while the protrusion 25 is formed on an outer side thereof.

On an inner circumferential surface of the main body 41, there are provided, as the aforesaid engaging portions, the fixing concave portion 30 for fixing the rod 43, a first regulating convex portion 47 and a second regulating convex portion 48 for regulating the backward movement of the rod 43.

(2) Operations and Effects

Figure 6A:
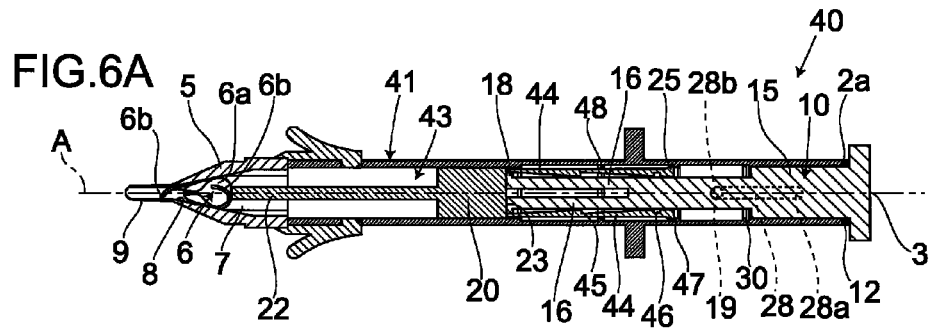
FIG. 6 is a diagram showing the intraocular lens inserting device in use in a stepwise manner according to the second embodiment, in which (a) is a section thereof illustrating the first push-out operation thereof, (b) illustrating a return to a position where the intraocular lens inserting device is operable, (c) illustrating the second push-out operation thereof, (d) illustrating a return to the position where the intraocular lens inserting device is operable, and (e) illustrating the third push-out operation thereof, respectively.

According to the foregoing structure, when the engagement between the protrusion 25 and the fixing concave portion 30 of the main body 41 is released by an external force applied to the operational portion 3 toward the forward direction at the time the operational portion 3 is being plunged into the main body 41, the plunger 10 and the rod 43 move together in the forward direction while compressing the coil spring 12, as shown in FIG. 6a.

At this moment, the plunger 10 allows the stopper pin 19 to move from the one end 28a toward the other end 28b within the sliding hole 28 provided in the main body 41. Thus, due to the stopper pin 19 reaching the other end 28b of the sliding hole 28, the plunger 10 and the operational portion 3 are allowed to mechanically stop at the push-out position.

At this time, while the rod 43 moves in the forward direction, the protrusion 25 is allowed to overcome the first regulating convex portion 47 of the main body 41 in such a way that the locking pieces 44 elastically deform toward the inside with respect to the lens advancing axis A.

Figure 6B:
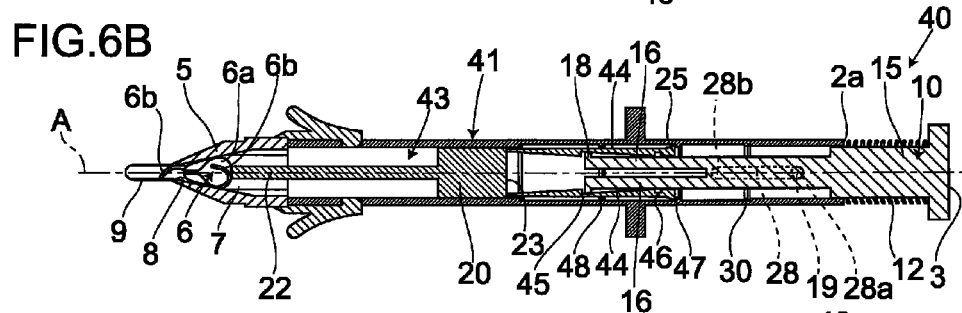

Then, when the external force applied to the operational portion 3 is released, as shown in FIG. 6(b), the plunger 10 is allowed to move in the backward direction by the biasing force of the coil spring 12. At this stage as well, the stopper pin 19 moves within the sliding hole 28 from the other end 28b (push-out position) to the one end 28a in the plunger 10.

In this way, when the plunger 10 moves from the push-out position toward the one end 28a, the push-out pieces 16, 16 move between inside of the locking pieces 44 in the backward direction. On the other hand, the backward movement of the rod 43 is regulated since the protrusions 25 of the locking pieces 44 engage with the first regulating convex portion 47 of the main body 41, and thus it is kept stopped. Then, the convex portion 18 of the push-out piece 16 is engaged with the first concave portion 45 of the locking piece 44. In this manner, the plunger 10 and the operational portion 3 return to the operable position.

Through the first operation described above, the rod 43 allows the lens contact portion 22a provided on the leading end of the push-out shaft 22 to abut on a circumference of the optical portion 6a of the intraocular lens 6 placed in the cartridge 5 to thereby push out the intraocular lens 6 in the forward direction. This causes the intraocular lens 6 to move from the lens placement portion 7 to the transition portion 8 in sequence and to stop at the transition portion 8.

Figure 6C:
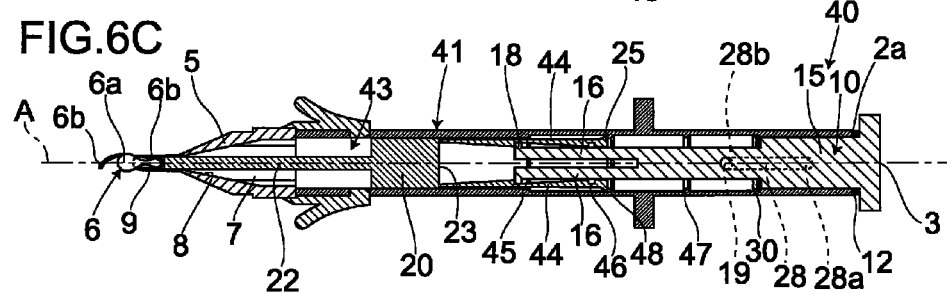

Next, as shown in FIG. 6(c), when the operational portion 3 returned back to the operable position is plunged again into the main body 41, the plunger 10 and the rod 43 are allowed to move together in the forward direction, since the convex portions 18 of the push-out pieces 16, 16 are engaged with the first concave portions 45 of the locking pieces 44.

At this stage as well, the stopper pin 19 of the plunger 10 moves from the operable position toward the other end 28b within the sliding hole 28 provided in the main body 41. Thus, when the stopper pin 19 reaches the other end 28b of the sliding hole 28, the plunger 10 and the operational portion 3 then mechanically stop at the push-out position again.

At this time, while the rod 43 moves in the forward direction, the protrusion 25 is allowed to overcome the second regulating convex portion 48 of the main body 41 in such a way that the locking pieces 44 elastically deforms toward the inside with respect to the lens advancing axis A.

Figure 6D:
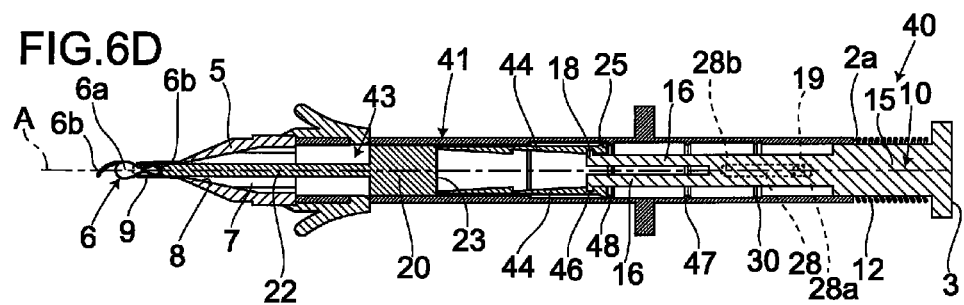

Then, when the external force applied to the operational portion 3 is released, as shown in FIG. 6(d), the plunger 10 is allowed to move in the backward direction by the biasing force of the coil spring 12. At this stage as well, the stopper pin 19 moves within the sliding hole 28 from the other end 28b (push-out position) to the one end 28a in the plunger 10.

In this way, when the operational portion 3 moves from the other end 28b (push-out position) toward the one end 28a, the push-out pieces 16, 16 move inside of the locking pieces 44 in the backward direction. On the other hand, the backward movement of the rod 43 is regulated since the protrusions 25 of the locking pieces 44 engage with the second regulating convex portions 48 of the main body 41 and thus it is kept stopped. Then, the convex portions 18 of the push-out pieces 16, 16 are engaged with the second concave portions 46 of the locking pieces 44. In this manner, the plunger 10 and the operational portion 3 return to the operable position again.

Through the second operation described above, the rod 43 allows the lens contact portion 22a provided on the leading end of the push-out shaft 22 to move the intraocular lens 6 placed inside the cartridge 5 from the transition portion 8 to the nozzle 9 in sequence and to stop at the predetermined position. According to the present embodiment, the intraocular lens inserting device 40 allows the lens contact portion 22a to stop once when the intraocular lens 6 is passed through the nozzle 9.

Figure 6E:
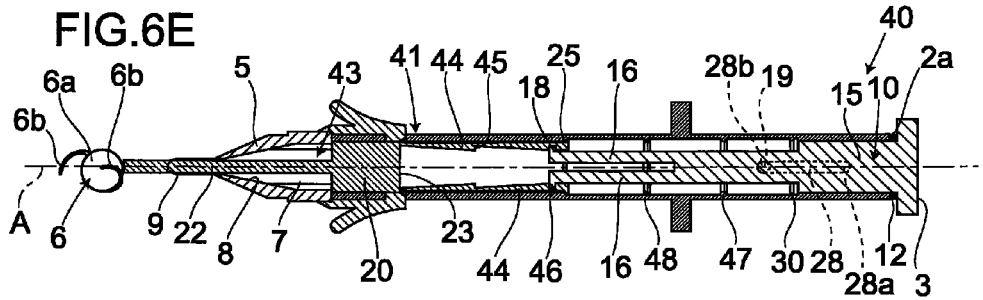

Next, as shown in FIG. 6(e), when the operational portion 3 returned back to the operable position is plunged again into the main body 41, the plunger 10 allows the rod 43 to move further in the forward direction, since the convex portions 18 of the push-out pieces 16, 16 are engaged with the second concave portions 46 of the locking pieces 44.

At this stage as well, the stopper pin 19 of the plunger 10 moves from the operable position toward the other end 28b within the sliding hole 28 provided in the main body 41. Thus, when the stopper pin 19 reaches the other end 28b of the sliding hole 28, the plunger 10 and the operational portion 3 then mechanically stop at the push-out position.

In this way, through the third operation of plunging the operational portion 3 returned back to the operable position into the main body 41 again, the push-out shaft 22 releases the intraocular lens 6 to the outside from the nozzle 9.

The intraocular lens inserting device 40 according to the present embodiment comprises the knock mechanism 42 automatically returning the operational portion 3 operable to push out the intraocular lens 6 to the operable position. Therefore, it is possible to achieve the same effect as the foregoing first embodiment.

Further, according to the present embodiment, the intraocular lens inserting device 40 is constituted so as to release the intraocular lens 6 to the outside by pushing out the operational portion 3 in the forward direction three times. Accordingly, the travel distance of the operational portion 3 can be reduced further, whereby the operator can easily adjust the travel distance of the intraocular lens 6.

Furthermore, the distance from the one end 28a to the other end 28b of the sliding hole 28, i.e., the travelling range of the stopper pin 19, is shortened, so that the distance from the one end 28a of the main body 41 to the operational portion 3 at the origin is also shortened. Therefore, when the lengths of the main body 41 and the push-out shaft 22 of the rod 43 are unchanged, the intraocular lens inserting device 40 can be downsized because the whole length thereof can be shortened.

3. Third Embodiment

The intraocular lens inserting device according to the present embodiment differs from the foregoing intraocular lens inserting device of the first embodiment in that the insertion tube comprises an inserting tubular portion. Incidentally, with the respect to the same structures as the foregoing structures, the same reference numbers are given to them and their descriptions are omitted.

Figure 7:
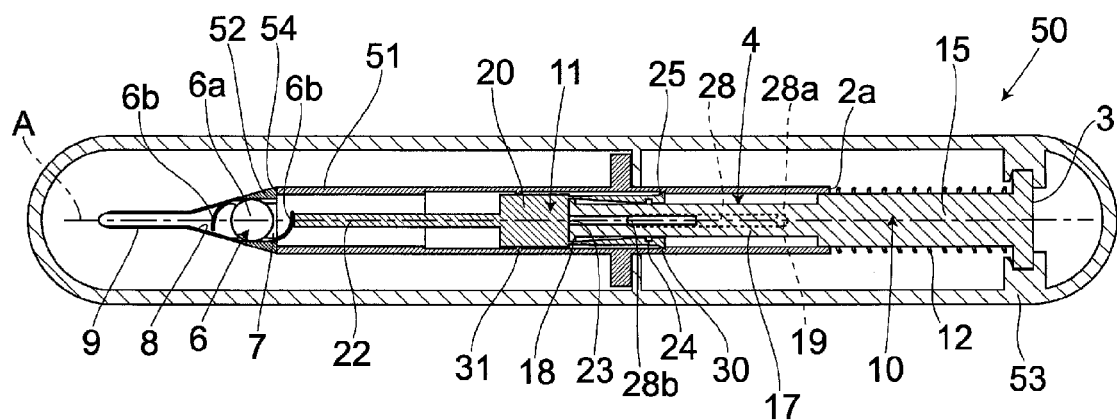
FIG. 7 is a cross-sectional view showing the overall structure of an intraocular lens inserting device according to a third embodiment of the invention, in which the intraocular lens inserting device is fixed in a casing.
Figure 8A:
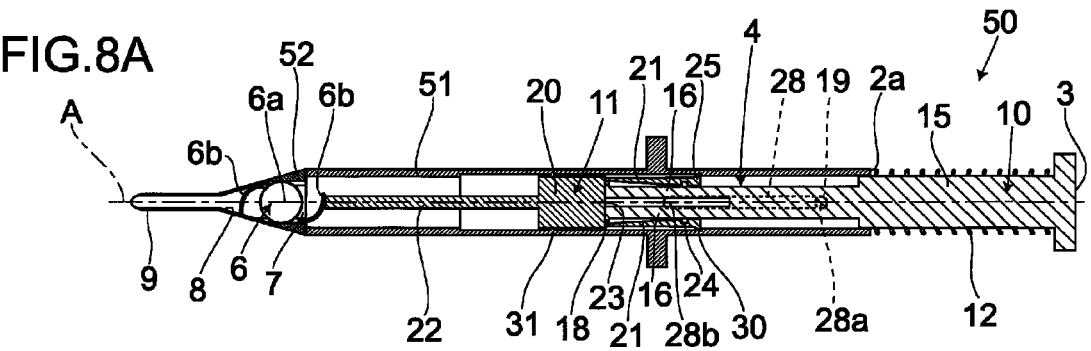
FIG. 8 is a diagram showing the intraocular lens inserting device in use in a stepwise manner according to the third embodiment, in which (a) is a section thereof illustrating the intraocular lens inserting device in an initial state, (b) illustrating the first push-out operation thereof, (c) illustrating a return to a position where the intraocular lens inserting device is operable, and (d) illustrating the second push-out operation thereof, respectively.
Figure 8B:
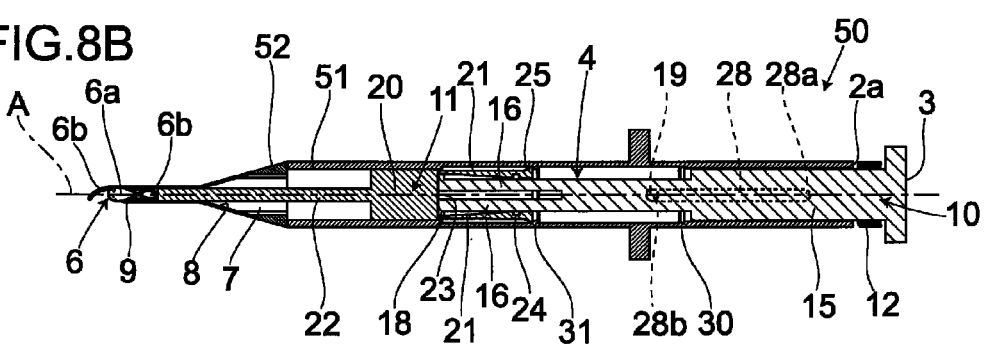
Figure 8C:
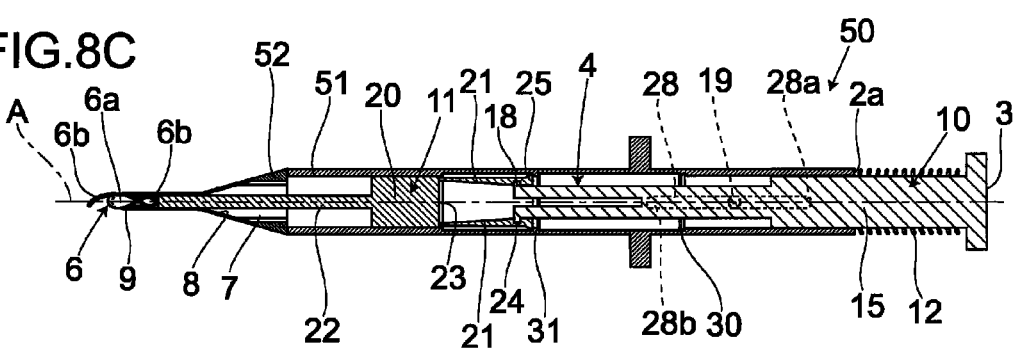
Figure 8D:
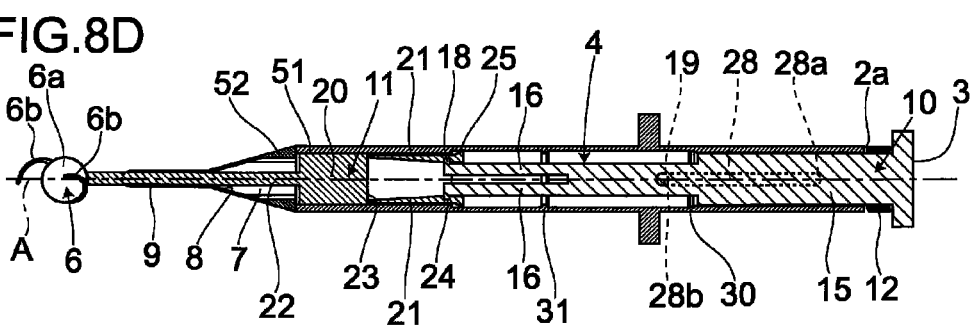

An intraocular lens inserting device 50 shown in FIG. 7 comprises a main body 51, the operational portion 3 and the knock mechanism 4. The main body 51 is provided with an inserting tubular portion 52 into which the intraocular lens 6 is placed in advance. The intraocular lens inserting device 50 is a pre-loaded typed one which is fixed in a casing 53, and transported after being packaged with the intraocular lens 6 being loaded therein.

The main body 51 is provided at its leading end with an attachment portion 54 for attaching the inserting tubular portion 52 instead of the rectangular receiving hole for installing the cartridge.

The inserting tubular portion 52 is provided with the lens placement portion 7, the transition portion 8 and the nozzle 9 in sequence along the lens advancing axis A. The inserting tubular portion 52 is integrated with the main body 51 with the intraocular lens 6 being placed therein beforehand. The inserting tubular portion 52 is structured such that the intraocular lens 6 placed on the lens placement portion 7 is pushed out by the rod 11 to allow the intraocular lens 6 to pass from the lens placement portion 7 through the transition portion 8, whereby the intraocular lens 6 is folded small to be able to be released from the nozzle 9 to the outside with the intraocular lens 6 being folded small. The inserting tubular portion 52 is attached, at its base end, to the attachment portion 54 of the main body 51 and is integrated therewith.

According to the foregoing structure, as shown in FIG. 8, the intraocular lens 6 can be released to the outside by performing the operation twice like in as the first embodiment. In addition, the operational portion 3 can be automatically returned to the operable position by the knock mechanism 4 during the operation.

The intraocular lens inserting device 50 according to the present embodiment comprises the knock mechanism 4 for automatically returning the operational portion 3 operable to push out the intraocular lens 6 to the operable position. Therefore, the intraocular lens inserting device 50 can achieve the same effect as that of the foregoing first embodiment.

Furthermore, according to the intraocular lens inserting device 50 of the present embodiment, it is possible to eliminate the needs for such works as loading of the intraocular lens 6 in the cartridge 5, attachment of the cartridge 5 to the main body 51, etc. during the surgery, so that mistakes of handling the intraocular lens inserting device 50 can be decreased.

Moreover, the intraocular lens inserting device 50 according to the present embodiment is provided as a disposable system using the main body 51, the intraocular lens 6 and the inserting tubular portion 52 only once. Therefore, a risk of infection disease can be dramatically decreased.

Additionally, the intraocular lens inserting device 50 according to the present embodiment is fixed in the casing 53 and packed, thereby prohibiting the plunger 10 from being unexpectedly plunged in the forward direction during the storage and transportation.

Incidentally, although the explanation has been given of the case where the intraocular lens 6 is released to the outside by the operation plunging the operational portion 3 forward twice, the invention is not limited thereto, but the intraocular lens 6 may be released to the outside by the operation plunging the operational portion 3 forward three times like in the foregoing second embodiment.

4. Other Embodiments

In the foregoing embodiments, although the explanation has been given of the case where a cross-sectional surface of an inner shape perpendicular to the lens advancing axis is circular, the invention is not limited to these cases, and the cross-sectional surface may be ellipse or polygon such as rectangular. In this case, the same shape corresponding to the inner shape of the main body may be chosen and applied to the shapes of other members of the knock mechanism, the axis body of the plunger and the sliding body of the rod.

In the foregoing embodiments, an explanation has been given of the example where the knock mechanism 4 comprises the plunger 10 integrated with the operational portion 3, the rod 11, the coil spring 12 as a biasing means biasing the plunger 10 toward the retreating or backward direction, and the engaging portions provided on the inner surface of the main body 2. The invention, however, is not limited thereto. As it would suffice if the knock mechanism 4 can automatically return the operational portion 3 to the operable position, the mechanical knock 4 may utilize another knock mechanism such as a mechanical pencil. In addition, the returning means is not limited to the coil spring, but a plate spring, elastic rubber, or the like may also be used.

In the foregoing embodiments, an explanation has been given of the example where the operation plunging the operational portion 3 forward is performed two or three times to release the intraocular lens to the outside. The invention, however, is not limited thereto, and the operation may be performed four, five or more times because it would suffice if the operations allow the operational portion 3 to automatically return to the operable position.

In the foregoing embodiments, an explanation has been given of the case where the lens contact portion is brought into a position protruded from the nozzle when the intraocular lens is released to the outside by the operation performed two or three times. The invention, however, is not limited thereto, and the lens contact portion may stay within the nozzle after the operation is performed two or three times so that the intraocular lens may be slowly released into the eye by its shape recovery ability coming from the elastic force of the intraocular lens itself even after the forward movement of the rod stops.

In the foregoing embodiments, an explanation has been given of the case where the operational portion is provided so as to be able to move back and forth parallel to the lens advancing axis. The invention, however, is not limited thereto, and the operational portion may be provided so as to be able to move back and forth perpendicular to the lens advancing axis. In this case, the operational portion may be provided, for example, on the lateral face of the main body, such that it may have the push-out position in an inner direction toward the main body (lens advancing direction) and has the origin in an outer direction away from the main body (retreating direction).

In the foregoing embodiments, an explanation has been given of the case where the transmitting portion is the plunger. The invention, however, is not limited thereto, and the transmitting portion may be a link mechanism, a cam mechanism or the like to thereby transmit the force applied to the operational portion to the lens contact portion.

In the foregoing embodiments, an explanation has been given of the case where the inserting tubular portion comprises the lens placement portion. The invention, however, is not limited thereto, and the inserting tubular portion has only to comprise the transition portion and the nozzle, and thus, in this case, the lens placement portion may be provided on the main body.

Incidentally, the present invention may be applied to various types of intraocular lens inserting devices, disclosed, for example, in Japanese Unexamined Patent Application Publication No. 2008-521535, Japanese Unexamined Patent Application Publication No. 2001-502563, German Patent Publication No. 4110278, Japanese Unexamined Patent Application Publication No. H04-212350 and Japanese Unexamined Patent Application Publication No. S63-197453.

The invention claimed is:

1. An intraocular lens insertion device, comprising:
   a main body with a lens advancement axis extending therethough;
   a rod that defines a length and is movable along the lens advancement axis in a forward direction from an initial pre-use position to a fully extended position;
   a plunger that defines a length and is movable relative to the main body along the lens advancement axis with the rod in the forward direction from a return position, which defines a proximal-most position of the plunger, to a push-out position, which defines a distal-most position of the plunger, and is movable relative to the main body along the lens advancement axis away from at least a portion of the rod in a rearward direction from the push-out position to the return position; and
   a bias element that biases the plunger to the return position by applying a force in the rearward direction to the plunger that drives the plunger to the return position;
   wherein the pre-use position of the rod, the return position of the plunger and the respective lengths of the rod and the plunger are such that a first movement of the plunger from the return position to the push-out position will result in only partial movement of the rod from the pre-use position to the fully extended position.

2. An intraocular lens insertion device as claimed in claim 1, wherein
   the rod includes a latch with a deflectable locking piece and a latch protrusion carried by the deflectable locking piece;
   the main body includes an inner surface and a concave region on the inner surface; and
   the latch protrusion is located within the concave region when the rod is in the pre-use position.

3. An intraocular lens insertion device as claimed in claim 2, wherein
   the main body includes a main body protrusion on the inner surface that is offset in the forward direction from the concave region; and
   the latch protrusion will pass over the main body protrusion during the first movement of the plunger from the return position to the push-out position.

4. An intraocular lens insertion device as claimed in claim 3, wherein
   the rod further includes a sliding body, defining a forward end and a rearward end, and a shaft extending forwardly from the forward end of the sliding body;
   the latch extends rearwardly from the rearward end of the sliding body;
   the plunger engages and pushes the rearward end of the sliding body during the first movement of the plunger from the return position to the push-out position; and
   the plunger pushes the latch during a second movement of the plunger from the return position to the push-out position that results in movement of the rod to the fully extended position.

5. An intraocular lens insertion device as claimed in claim 4, wherein
   the plunger disengages from the rearward end of the sliding body as the plunger moves in the rearward direction from the push-out position to the return position.

6. An intraocular lens insertion device as claimed in claim 1, wherein
   the main body is configured to receive a cartridge.

7. An intraocular lens insertion device as claimed in claim 1, further comprising:
a cartridge;
wherein the main body is configured to receive the cartridge.

8. An intraocular lens insertion device as claimed in claim 1, wherein
the main body includes an integral lens placement portion, transition portion and nozzle.

9. An intraocular lens insertion device as claimed in claim 8, further comprising:
an intraocular lens stored in the lens placement portion.

10. An intraocular lens insertion device as claimed in claim 1, wherein
the bias element comprise a coil spring.

11. An intraocular lens insertion device as claimed in claim 1, wherein
the main body defines a rearward end; and
the bias element is located between the rearward end of the main body and a portion of the plunger.

12. An intraocular lens insertion device as claimed in claim 1, wherein
the plunger and the rod are not secured to one another.

13. An intraocular lens insertion device, comprising
a main body with a lens advancement axis extending therethough;
a rod that defines a length and is movable along the lens advancement axis in a forward direction from an initial pre-use position to a fully extended position;
a plunger that defines a length and is movable relative to the main body along the lens advancement axis with the rod in the forward direction from a return position to a push-out position and is movable relative to the main body along the lens advancement axis away from at least a portion of the rod in a rearward direction from the push-out position to the return position; and
a bias element that biases the plunger to the return position by applying a force in the rearward direction to the plunger that drives the plunger to the return position;
wherein the pre-use position of the rod, the return position of the plunger and the respective lengths of the rod and the plunger are such that a first movement of the plunger from the return position to the push-out position will result in only partial movement of the rod from the pre-use position to the fully extended position; and
wherein the respective lengths of the rod and the plunger are such that a second movement of the plunger from the return position to the push-out position will result in movement of the rod to the fully extended position.

\* \* \* \* \*